US011828760B2

(12) United States Patent
Albitar

(10) Patent No.: US 11,828,760 B2
(45) Date of Patent: Nov. 28, 2023

(54) HEMATOPOIETIC CELL PHENOTYPING USING CIRCULATING CELL-FREE MARKERS

(71) Applicant: Quest Diagnostics Investments LLC, Secaucus, NJ (US)

(72) Inventor: Maher Albitar, Coto De Caza, CA (US)

(73) Assignee: Quest Diagnostics Investments LLC, Secaucus, NJ (US)

( * ) Notice: Subject to any disclaimer, the term of this patent is extended or adjusted under 35 U.S.C. 154(b) by 176 days.

(21) Appl. No.: 16/118,874

(22) Filed: Aug. 31, 2018

(65) Prior Publication Data

US 2019/0064170 A1   Feb. 28, 2019

Related U.S. Application Data

(63) Continuation of application No. 14/992,505, filed on Jan. 11, 2016, now Pat. No. 10,067,133, which is a continuation of application No. 12/297,389, filed as application No. PCT/US2006/003238 on Aug. 17, 2006, now Pat. No. 9,255,926, which is a continuation of application No. 11/206,260, filed on Aug. 17, 2005, now abandoned.

(51) Int. Cl.
*G01N 33/574* (2006.01)
*G01N 33/68* (2006.01)

(52) U.S. Cl.
CPC . *G01N 33/57426* (2013.01); *G01N 33/57488* (2013.01); *G01N 33/6869* (2013.01); *G01N 2333/7051* (2013.01); *G01N 2333/70503* (2013.01); *G01N 2333/70514* (2013.01); *G01N 2333/70517* (2013.01); *G01N 2333/70596* (2013.01); *G01N 2800/56* (2013.01)

(58) Field of Classification Search
CPC ... G01N 33/57426; G01N 2333/70503; G01N 2333/7051; G01N 2333/70596; G01N 2800/56; G01N 33/57488; G01N 33/6869
See application file for complete search history.

(56) References Cited

U.S. PATENT DOCUMENTS

| | | |
|---|---|---|
| 4,956,778 A | 9/1990 | Naito |
| 5,091,513 A | 2/1992 | Huston et al. |
| 5,132,405 A | 7/1992 | Huston et al. |
| 5,234,816 A | 8/1993 | Terstappen |
| 5,292,636 A | 3/1994 | Kung et al. |
| 5,605,805 A | 2/1997 | Verwer et al. |
| 7,718,387 B2 | 5/2010 | Albitar et al. |
| 7,943,332 B2 | 5/2011 | Albitar et al. |
| 2002/0019018 A1 | 2/2002 | Christopherson et al. |
| 2003/0068664 A1 | 4/2003 | Albitar et al. |
| 2003/0099650 A1 | 5/2003 | Ho et al. |
| 2011/0236994 A1 | 9/2011 | Albitar et al. |

FOREIGN PATENT DOCUMENTS

| | | |
|---|---|---|
| WO | WO-98/20155 A1 | 5/1998 |
| WO | WO-2005/103719 | 11/2005 |

OTHER PUBLICATIONS

Rosenwaar et al. Biologic activities of IL-1 and its role in human disease, Journal of Allergy and Clinical immunology, vol. 102, p. 344-350. (Year: 1998).*
Duensing et al., Elevated plasma levels of of interleukin-1 receptor antagonist are associated with decreased cellular BCL-2 oncoprotein expression in B-Chronic lymphocytic leukemia , vol. 13, p. 383-385. (Year: 1998).*
Ebrahimi et al., Cytokines in pancreatic carcinoma, correlation with phenotypic characteristics and prognosis, Cancer, vol. 101, p. 2727-2736. (Year: 2004).*
Albitar et al., Free Circulating Soluble CD52 as a Tumor Marker in Chronic Lymphocytic Leukemia and Its Implication in Therapy with Anti-CD52 Antibodies, Cancer, Sep. 1, 2004, pp. 999-1008, vol. 101, No. 5.
Babusikova et al., Flow cytometry of peripheral blood and bone marrow cells from patients with hairy cell leukemia: phenotype of hairy cells, lymphocyte subsets and detection of minimal residual disease after treatment, Neoplasma., 2001, pp. 350-357, vol. 48, No. 5.
Bardin et al., Soluble CD146, a novel endothelial marker, is increased in physiopathological settings linked to endothelial junctional alteration, Thromb Haemost, 2003, pp. 915-920, vol. 90, No. 5.
Belov et al., Immunophenotyping of leukemias using a cluster of differentiation antibody microarray. Liquid Crystals, 61(11): 4483-4489, 2001. (XP001080150).
Belov et al., Screening microarrays of novel monoclonal antibodies for binding to T-, B- and myeloid leukaemia cells. Journal of Immunological Methods, 305(1): 10-19, 2005. (XP005106058).

(Continued)

*Primary Examiner* — Taeyoon Kim
*Assistant Examiner* — Tiffany M Gough
(74) *Attorney, Agent, or Firm* — Foley & Lardner LLP

(57) ABSTRACT

The present invention provides methods of classifying cluster of differentiation (CD) marker phenotype for hematopoietic cancer cells using multiple circulating cell-free CD markers in bodily fluid. In other aspects, treatment and disease progression of particular hematopoietic cancers can be monitored by measuring the levels of CD and other markers in bodily fluids of a patient.

11 Claims, 3 Drawing Sheets

(56) References Cited

OTHER PUBLICATIONS

Digiuseppe and Borowitz, Clinical utility of flow cytometry in the chronic lymphoid leukemias. Seminars in Oncology, 25(1): 6-10, 1998. (XP002200401).
Elghetany, Surface marker abnormalities in myelodysplastic syndromes, Haematologica, 1998, vol. 83, p. 1104-1115.
Extended European search report for EPO Patent Application No. 06813547.4.
Foschi et al., Soluble CD30 Serum Level in HCV-Positive Chronic Active Hepatitis: A Surrogate Marker of Disease Activity?, Cytokine, Jun. 2000, pp. 815-818, vol. 12, No. 6.
Frickhofen et al., Rearranged Ig Heavy Chain DNA Is Detectable in Cell-Free Blood Samples of Patients With B-Cell Neoplasia, Blood, Dec. 15, 1997, pp. 4953-4960, vol. 90, No. 12.
Giles et al., Circulating CD20 and CD52 in patients with non-Hodgkin 19s lymphoma or Hodgkin 19s disease, British Journal of Haematology, 2003, pp. 850-857, vol. 23.
Heintel et al., Association of CD38 Antigen Expression with Other Prognostic Parameters in Early Stages of Chronic Lymphocytic Leukemia, Leukemia & Lymphoma, 2001, pp. 1315-1321, vol. 42.
Hock et al., The Clinical Significance of Soluble CD86 Levels in Patients with Acute Myeloid Leukemia and Myelodysplastic Syndrome, Cancer, Oct. 15, 2003, pp. 1681-1688, vol. 98, No. 8.
Hofmann et al., Avidin-Biotin Affinity Columns, General Methods for Attaching Biotin to Peptides and Proteins, Journal of the American Chemical Society, May 24, 1978, pp. 3585-3590, vol. 100, No. 11.
Hulkkonen et al., "Interleukin-1, interleukin1 receptor antagonist and interleukin-6 plasma levels and cytokine gene polymorphisms in chronic lymphocytic leukemia: correlation with prognostic parameters," Haematologica, 2000, 85:600-606.
Huston et al., Protein engineering of antibody binding sites: Recovery of specific activity in an anti-digoxin single-chain Fv analogue produced in *Escherichia coli*, Proc. Natl. Acad. Sci. USA, Aug. 1988, pp. 5879-5883, vol. 85.
Ibrahim et al., CD38 expression as an important prognostic factor in B-cell chronic lymphocytic leukemia, Blood, Jul. 1, 2001, pp. 181-186, vol. 98, No. 1.
Iizuka et al., Serum soluble CD4, CD8 and IL-2 levels in adult acute myeloid leukemia in remission, Med Oncology and Tumor Pharmacotherapy, vol. 9, 1992, p. 57-64.
International Search Report dated Aug. 3, 2007 for PCT/US2006/032388.
Ishibe et al., CXCR4 expression is associated with survival in familial chronic lymphocytic leukemia, but CD38 expression is not, Blood, Aug. 1, 2002, pp. 1100-1101, vol. 100, No. 3.
Jilani et al., Differences in CD33 intensity between various myeloid neoplasms, Am J Clin Pathol, Oct. 2002, pp. 560-566, vol. 118, No. 4.
Khalidi et al., The Immunophenotype of adult acute myeloid leukemia: High frequency of lymphoid antigen expression and comparison of immunophenotype, French-American-British classification, and karyotypic abnormalities. Am J Clin Pathology, 109:211-220, 1998. (XP002200399).
Kitagawa et al., Enzyme Coupled Immunoassay of Insulin Using a Novel Coupling Reagent, J. Biochem., 1976, pp. 233-236, vol. 79.
Manshouri et al., Circulating CD20 is detectable in the plasma of patients with chronic lymphocytic leukemia and is of prognostic significance, Blood, Apr. 1, 2003, pp. 2507-2513, vol. 101, No. 7.
Matsushita et al., Elevated levels of soluble CD163 in sera and fluids from rheumatoid arthritis patients and inhibition of the shedding of CD163 by TIMP-3, Clin Exp Immunol., Oct. 2002, pp. 156-161, vol. 130, No. 1.
Moller et al., Soluble CD163: a marker molecule for monocyte/macrophage activity in disease, Scand J Clin Lab Invest Suppl., 2002, pp. 29-33, vol. 237.
Niitsu et al., High serum soluble CD44 is correlated with a poor outcome of aggressive non-Hodgkin 19s lymphoma, Leukemia Research, 2002, pp. 241-248, vol. 26.
Onji et al., Serum levels of soluble CD4 and CD8 in patients with chronic viral hepatitis, Hepatogastroenterology, 1994, abstract.
Orfao et al., Clinically Useful Information Provided by the Flow Cytometric Immunophenotyping of Hematological Malignancies: Current Status and Future Directions, Clinical Chemistry, 1999, pp. 1708-1717, vol. 45, No. 10.
Paidas et al., Soluble monocyte cluster domain 163, a new global marker of anti-inflammatory response, is elevated in the first trimester of pregnancy, J Thromb Haemost., Jun. 2004, pp. 1009-1010, vol. 2, No. 6.
Pui et al., Serum CD4, CD8 and interleukin-2 Receptor levels in childhood acute myeloid leukemia, Leukemia, vol. 5, 1991, p. 249-254.
Pui et al., Serum levels of CD8 antigen in childhood lymphoid malignancies: A possible indicator of increased suppressor cell activity in poor-risk patients, Blood, vol. 72, 1988, p. 1015-1021.
Rothe et al., Consensus protocol for the flow cytometric immunophenotyping of hematopoietic malignancies, Leukemia, 1996, pp. 877-895, vol. 10.
Saussoy et al., Differentiation of acute myeloid leukemia from B- and T-Lineage acute lymphoid leukemias by real-time quantitative reverse transcription-PCR of lineage marker mRNAs. Clinical Chemistry, 50(7): 1165-1173, 2004. (XP002509024).
Schaer et al., Soluble hemoglobin-haptoglobin scavenger receptor CD163 as a lineage-specific marker in the reactive hemophagocytic syndrome, European Journal of Haematology, Jan. 2005, pp. 6-10, vol. 74, No. 1.
Scrivener et al., Analysis of the expression of critical activation/interaction markers on peripheral blood T cells in B-cell chronic lymphocytic leukaemia: evidence of immune dysregulation, British Journal of Haematology, Mar. 2001, pp. 959-964, vol. 112, No. 4.
Symenoidis et al., Immune funcation parameters at diagnosis in patients with myelodysplastic syndromes: Correlation with the FAB classification and prognosis, European Journal of Haemotology, 1991, vol. 41, p. 277-281.
Office Action issued in U.S. Appl. No. 11/206,260, dated Jul. 14, 2009.
Office Action issued in U.S. Appl. No. 11/206,260, dated Mar. 3, 2008.
Office Action issued in U.S. Appl. No. 11/206,260, dated Oct. 30, 2008.
Office Action issued in U.S. Appl. No. 11/206,260, dated Oct. 5, 2007.
Wagner et al., Chronic lymphocytic leukaemia: new biological markers for assessing prognosis, The Hematology Journal, 2004, pp. 197-201, vol. 5, No. 3.
Office Action issued in U.S. parent U.S. Appl. No. 12/297,389, dated Mar. 27, 2012.
Office Action issued in U.S. Appl. No. 12/297,389, dated Nov. 1, 2012.
Office Action issued in U.S. Appl. No. 12/297,389, dated Jun. 4, 2013.
Office Action issued in U.S. Appl. No. 12/297,389, dated Apr. 7, 2015.
Notice of Allowance issued in U.S. Appl. No. 12/297,389, dated Sep. 20, 2015.
Office Action issued in U.S. Appl. No. 14/992,505, dated Oct. 3, 2017.
Notice of Allowance issued in U.S. Appl. No. 14/992,505, dated May 7, 2018.

\* cited by examiner

HEMATOPOIETIC CELL PHENOTYPING USING CIRCULATING CELL-FREE MARKERS

FIELD OF THE INVENTION

The present invention relates to the determination of the cell surface cluster of differentiation (CD) antigen phenotype of a hematopoietic disorder.

BACKGROUND OF THE INVENTION

The following description is provided to assist the understanding of the reader. None of the information provided or references cited is admitted to be prior art to the present invention.

Cluster of differentiation (CD) markers have been established to define human leukocyte differentiation antigens (Bernard and Boumsell, Hum Immunol 11(1):1-10, 1984) by the comparison of reactivities of monoclonal antibodies directed against these antigens. These antigens are expressed on the cell surface of leukocytes and, therefore, serve as markers of cell lineage and distinguish populations of leukocytes with different functions, e.g., neutrophils and monocytes.

Leukocyte cell-surface antigens are widely used clinically for the identification of leukocyte populations and their functional status (Krensky et al., Clin Immunol Rev 4(1): 244-9, 1985; Kung et al., Int J Dermatol 22(2):67-74, 1983; Cosimi et al., Urol Clin North Am 10(2):289-99, 1983; Knowles et al., Diagn Immunol 1(3):142-9, 1983; and Hoffman et al., Clin Lab Haematol 6(4):383-6, 1984). For example, T cells are typically associated with the expression of specific CD markers such as CD2, CD3, CD5, and CD7, while CD4 and CD8 are associated with helper T cells and cytotoxic cells or suppressor cells, respectively. Similarly, B cells are associated the expression of, for example, CD19 and CD20. Furthermore, many leukemias and lymphomas have been associated with a particular complement of antigen expression on the cell surface of a patient's leukocytes (Rothe et al. Leukemia 10(5):877-95, 1996). This complement of antigens is the CD marker phenotype of that leukocyte and is a basis for identification of the specific leukemia or lymphoma.

CD markers are typically assayed through immunoassays (i.e., assays employing specific antibodies for the detection of antigen). These assays allow the detection of specific antigens based upon the specificity of interaction between a particular antigen and a labeled (e.g., with a fluorescent label) antibody. In general, the specific complement of CD markers expressed on the cell surface of the leukocyte is detected directly using intact leukocytes, labeling the particular CD markers with fluorescently-labeled, marker-specific antibodies and detection using flow cytometry.

It has been recently shown that some CD markers expressed on the surface of leukocytes are circulating free from intact cells in bodily fluids and can be detected by immunoassay. Furthermore, other studies have shown an association between soluble CD markers, as detected by ELISA, and disease staging or monitoring progression (Manshouri T, et al., Blood. 2003 Apr. 1:101(7):2507-13. Epub 2002 Nov. 21; Heintel D, et al., Leuk. Lymphoma. 2001 November-December; 42(6):1315-21; Foschi F G, et al., Cytokine. 2000 June; 12(6):815-8; Bardin N, et al., Thromb Haemost. 2003 November; 90(5):915-20; Niitsu N, Iijima K., Leuk Res. 2002 March; 26(3):241-8; Albitar M, et al., Cancer. 2004 Sep. 1; 101(5):999-1008; and Hock B D, et al., Cancer. 2003 Oct. 15; 98(8):1681-8), US Patent Publication 2003/0068664, Apr. 10, 2003, and U.S. Pat. No. 5,426,029.

SUMMARY OF THE INVENTION

The present invention provides methods of identifying the CD marker phenotype of hematopoietic cells which are involved in a pathologic condition or disease. In preferred embodiments, a test sample(s) of patient bodily fluid are assayed using antibodies specific to a panel of CD markers to determine a CD phenotype. The CD markers are detected in the bodily fluid as opposed to being detected in association with viable cells. This phenotype can be used to identify the patient's particular proliferative disorder as well as to determine an appropriate treatment regimen or to determine the progression or prognosis of the disorder. In a preferred embodiment, the CD markers to be detected are characterized in not being actively secreted or actively shed by hematopoietic cells.

According to one aspect of the present invention, there are provided methods of identifying a CD phenotype of hematopoietic cells associated with a disease or disorder in an individual, the disease or disorder selected from the group consisting of a hematopoietic proliferative disorder, autoimmune disease, and infection. In this method, a level of two or more CD markers circulating in a bodily fluid sample from said individual is determined. The level of each determined CD marker is compared to the level of that CD marker in a bodily fluid of a normal individual. The CD phenotype is then determined for the hematopoietic cells of the individual which underlie a disease or condition determined by assigning markers, for which the levels in the bodily fluid of the patient deviate from the levels in a normal individual.

As used herein the phrase "hematopoietic cells associated with a disease or disorder" refers to a population of hematopoietic cells that is causally or non-causally connected with the disease or disorder. "Causally" refers to the situation in which that population of cells causes one or more symptoms of the disease or disorder. "Non-causally" refers to the situation in which that population of cells does not cause one or more symptoms of the disease or disorder, rather, that population of cells is itself a symptom or indicator of the disease or disorder.

If the disease or disorder is a hematopoietic proliferative disorder, the disease or disorder may be any of lymphocytic leukemia, acute myelogenous leukemia, acute lymphoblastic leukemia, myelodysplastic syndrome, chronic myelomonocytic leukemia, juvenile myelomonocyte leukemia, multiple myeloma, lymphoma, T-cell chronic lymphocytic leukemia, prolymphocytic leukemia, hairy cell leukemia, follicular lymphoma, lymphoplasmocytic immunocytoma, plasma cell leukemia, T prolymphocytic leukemia, mycosis fungoides, large granular lymphocyte leukemia, or adult T cell leukemia.

In some embodiments, the disease or disorder is an autoimmune disease, preferably the disease or disorder is any of ulcerative colitis, polyarteritis, pemphigus complex and systemic lupus erythematosus.

In other embodiments, the disease or disorder is an infection. In preferred embodiments, the infection is human immunodeficiency virus (HIV) infection.

A panel of CD markers that can be used to determine a CD phenotype in accordance with the methods of the invention are two more. In a preferred embodiment, if only two CD markers are evaluated, then the two CD markers are not CD20 and CD52. The number of CD markers that can be tested is simply limited by the number of CD markers known for which antibodies or other detection agents are available. In a preferred embodiment, only two CD markers are evaluated. The number of CD markers evaluated in a single bodily fluid may easily include three, four, five, six, seven or even more CD markers.

According to another aspect of the present invention, there are provided methods of identifying a patient's specific hematopoietic tumor type using the circulating cell-free CD marker phenotype. In this method, a sample of bodily fluid from a patient with a hematopoietic proliferative disorder is assayed for the levels of two or more CD markers. These levels are compared to the levels of the same markers as obtained from a corresponding bodily fluid of a normal individual. A phenotype for the proliferative disorder is determined by assigning markers, for which the levels in the bodily fluid of the patient are increased over the levels in a normal individual, to the patient's cellular phenotype. This phenotype is then compared to the cell-surface CD marker phenotype of known tumor types (see, for example, Tables 1 and 2) to classify the patient's tumor type. The phenotype can be further used in the determination of prognosis and/or treatment of the disorder. In a preferred embodiment, if only two CD markers are evaluated, then the two CD markers are not CD20 and CD52.

According to yet another aspect of the present invention, there are provided methods of monitoring treatment or progression of a hematopoietic proliferative disorder, an autoimmune disorder or an infection in a patient. In this method, a first sample of bodily fluid is obtained from a patient at the outset of monitoring or prior to treatment. This sample is assayed for two or more CD markers to determine the levels in the body at that time. A second sample of bodily fluid is obtained subsequent to the first sample or following or during treatment. This second sample is assayed for CD markers. The levels of the markers in the body at the two times are compared to each other. An increase in the levels in the second sample relative to the first sample indicates progression of the disease while a decrease indicates regression of the disease.

According to still another aspect of the present invention, there are provided methods of monitoring treatment or progression of acute myeloid leukemia (AML) or myelodysplastic syndrome (MDS) in a patient, wherein the method comprising determining the level of at least one circulating cell-free CD marker in a bodily fluid sample from the patient, wherein said at least one marker is selected from the group consisting of CD4, CD8, CD33, and CD34. In some embodiments, the one or more marker comprises CD4, CD8, CD33, and CD34. In preferred embodiments the one or more marker comprises CD4 and CD8. In other embodiments, the one or more marker comprises CD33. In still other embodiments, the one or more marker comprises CD34.

In some embodiments of the above aspect of the invention, the level of at least one circulating cell-free CD marker in a first bodily fluid sample is increased relative to the level of a corresponding circulating cell-free CD marker in a bodily fluid sample of a normal individual. In other embodiments of the above aspects of the invention, the level of at least one circulating cell-free CD marker in a first bodily fluid sample is decreased relative to the level of a corresponding circulating cell-free CD marker in a bodily fluid sample of a normal individual.

In other embodiments of the above aspect of the invention, the method further comprises, determining the level of at least one circulating cell-free CD marker in a second bodily fluid sample from the patient, wherein the second bodily fluid sample is taken after said first bodily fluid sample, and wherein said at least one marker is selected from the group consisting of CD4, CD8, CD33, and CD34; and comparing the level of said at least one marker in said first bodily fluid sample to the level of a corresponding CD marker determined for said second bodily fluid sample, wherein an increase in the level of a marker in said second bodily fluid sample relative to said corresponding marker in said first bodily fluid sample is indicative of progression of the disease or disorder, or wherein a decrease in the level of a marker in said second bodily fluid sample relative to said corresponding marker in said first bodily fluid sample is indicative of a regression of the disease or disorder.

According to still another aspect of the present invention, there are provided methods of monitoring treatment or progression of chronic lymphocytic leukemia, wherein the method comprising determining the level of at least one circulating cell-free marker in a bodily fluid sample from the patient, wherein said at least one marker is selected from the group consisting of CD3, CD5, interleukin-1 receptor antagonist (IL-1Ra), and interleukin-1β (IL-1β). In some embodiments, the one or more marker comprises CD3. In other embodiments, the one or more marker comprises CD5. In some embodiments, the one or more marker comprises interleukin-1 receptor antagonist (IL-1Ra). In other embodiments, the one or more marker comprises interleukin-1β (IL-1β). In preferred embodiments the one or more marker comprises CD3 and CD5. In other preferred embodiments the one or more marker comprises IL-1Ra and IL-1β. In still other embodiments, the one or more marker comprises CD3, CD5, interleukin-1 receptor antagonist (IL-1Ra), and interleukin-1β (IL-1β).

In some embodiments of the above aspect of the invention, the level of at least one circulating cell-free marker in a first bodily fluid sample is increased relative to the level of a corresponding circulating cell-free marker in a bodily fluid sample of a normal individual. In other embodiments of the above aspects of the invention, the level of at least one circulating cell-free marker in a first bodily fluid sample is decreased relative to the level of a corresponding circulating cell-free marker in a bodily fluid sample of a normal individual.

In other embodiments of the above aspect of the invention, the method further comprises, determining the level of at least one circulating cell-free marker in a second bodily fluid sample from the patient, wherein the second bodily fluid sample is taken after said first bodily fluid sample, and wherein said at least one marker is selected from the group consisting of CD3, CD5, interleukin-1 receptor antagonist (IL-1Ra), and interleukin-1β (IL-1β); and comparing the level of said at least one marker in said first bodily fluid sample to the level of a corresponding CD marker determined for said second bodily fluid sample, wherein an increase in the level of a marker in said second bodily fluid sample relative to said corresponding marker in said first bodily fluid sample is indicative of progression of CLL, or wherein a decrease in the level of a marker in said second bodily fluid sample relative to said corresponding marker in said first bodily fluid sample is indicative of a regression of CLL.

One of skill in the art would readily recognize that the measurement of multiple CD markers can be accomplished using various types of assays well-known in the art. In preferred embodiments, the CD marker is detected using a specific binding agent, preferably an antibody. In another embodiment, the assay is an immunoassay such as an enzyme-linked immunosorbent assay (ELISA) or sandwich-type ELISA. These assays are particularly amenable to the detection of multiple antigens. In another embodiment, the assay can be flow cytometry. In the later case, a sandwich-type assay involving capture of an antibody-antigen complex on a bead or microparticle and binding of a labeled second antibody can provide useful assay materials to be evaluated by flow cytometry.

The phrase "CD marker" as used herein refers to markers associated with a cell, as recognized by specific sets of antibodies, which used to identify the cell type, stage of differentiation and activity state of a cell. Preferred CD markers are those that are cell-surface expressed. There are currently 289 known CD markers, a complete listing of which can be found through public databases such as the Swiss-Prot Protein Knowledgebase (a collaboration between the Swiss Institute of Bioinformatics and the EMBL Out-station—the European Bioinformatics Institute; CDLIST.TXT). CD marker proteins are expressed on the surface of leukocytes and other cells.

As used herein, the phrase "CD phenotype" and "CD marker phenotype" are interchangeable and refer to the particular group of CD markers expressed on the cell surface of hematopoietic cells (e.g. leukocyte or lymphocyte). The phenotype may be determined through direct analysis of cell surface expression or through analysis of markers circulating in bodily fluid.

The phrase "corresponding CD marker" as used herein refers to the same CD marker measured in a corresponding body fluid sample from two individuals. The level of a corresponding CD marker is preferably a particular CD marker measured, for example, in a bodily fluid sample from a patient and a bodily fluid sample from a normal individual. The bodily fluid samples from the two individuals are preferably the same type of bodily fluid (e.g. serum from both individuals).

The phrase "identifying the CD phenotype by assigning any individual CD marker having a level different from the level of the corresponding CD marker in the bodily fluid of a normal individual to the phenotype" means that the CD phenotype is assigned by taking into account the CD marker level in the patient that is different from the level of the marker determined in the same bodily fluid of normal individuals using the same assay format. In this context, difference in the level refers to a statistically significant difference of the patient circulating cell-free CD marker over that typically measured for normal individuals. Such statistical analysis is well known in the art. See e.g., Giles et al., Br. J. Haematol. 123:1-8 (2003); Manshouri et al., Blood 101(7) 2507 (2003). A level for a particular CD marker that is different from the level of that CD marker in the same body fluid and detected with the same assay is generally an increase or a decrease of two fold, more preferably 3 fold, more preferably four fold and even more preferably 5 fold or more relative to that for normal individuals.

The term "circulating cell-free" used in reference to CD and other markers refers to markers that are present in the liquid phase of a bodily fluid and which remain in the liquid phase after cells have been removed from the bodily fluid. The marker may be shed from the cell or the cell surface or secreted from the cell and may be soluble in the liquid phase of the bodily fluid. Circulating cell-free CD markers may be a fragment of the native cell associated CD marker. Circulating cell-free CD markers may be physically associated with other biomolecules in body fluid.

A CD marker that is not actively secreted or actively shed from cells can be determined by methods well known in the art. For example, hematopoietic cells to be evaluated can be cultured with an agent that enhances active shedding of markers. An increase in the amount of the marker shed into the culture medium after exposure to the agent indicates that the marker is actively secreted or shed by the cells. An agent that increases shedding of CD markers is phorbol 12-myristate 13-acetate (PMA). See e.g., Manshouri et al., Blood 101(7) 2507 (2003), FIG. 4 and related text. HLA class 1 protein can be used as a positive control marker for active shedding.

In some embodiments the two or more CD markers are selected from the group consisting of CD3, CD4, CD5, CD7, CD8, CD10, CD11c, CD19, CD20, CD22, CD23, CD25, CD30, CD31, CD33, CD34, CD38, CD44, CD52, CD56, CD57, CD86, CD103, CD146, and CD163. In other embodiments, the two ore more CD markers are selected from the group consisting CD20, CD23, CD30, CD31, CD44, CD52, CD86, CD146, and CD163. In still other embodiments, the two ore more CD markers are selected from the group consisting CD5, CD10, CD11c, CD19, CD20, CD22, CD23, CD25, CD38, and CD103. In yet other embodiments, the two ore more CD markers are selected from the group consisting CD3, CD4, CD5, CD7, CD8, CD56, and CD57. In further embodiments, the two ore more CD markers are selected from the group consisting CD20, CD52, and CD86.

The phrase "specific binding agent" as used herein refers to any agent, molecule, or compound that specifically binds a CD marker or portion thereof. Examples include, but are not limited to, antibodies or antibody fragments, ligands, or receptors. These binding agents could be naturally occurring or synthetic and include modified or recombinant proteins. In preferred embodiments the specific binding agent is an antibody.

The term "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. An antibody can be specific for a particular antigen. The antibody or its antigen can be either an analyte or a binding partner.

Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies, more preferably single chain Fv (scFv) antibodies in which a variable heavy and a variable light chain are joined together (directly or through a peptide linker) to form a continuous polypeptide.

A single chain Fv ("scFv") polypeptide is a covalently linked VH:VL heterodimer which may be expressed from a nucleic acid including VH- and VL-encoding sequences either joined directly or joined by a peptide-encoding linker. Huston, et al. (1988) Proc. Nat. Acad. Sci. USA, 85:5879-5883. A number of structures for converting the naturally aggregated—but chemically separated light and heavy polypeptide chains from an antibody V region into an scFv molecule which will fold into a three dimensional structure substantially similar to the structure of an antigen-binding site. See, e.g. U.S. Pat. Nos. 5,091,513 and 5,132,405 and 4,956,778.

An "antigen-binding site" or "binding portion" refers to the part of an immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs." Thus, the term "FR" refers to amino acid sequences that are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and light chains are referred to as "complimentarily determining regions" or "CDRs" and are characterized, for example by Kabat et al. Sequences of proteins of immunological interest, 4th ed. U.S. Dept. Health and Human Services, Public Health Services, Bethesda, Md. (1987). An epitope is that portion of an antigen that interacts with an antibody.

The phrases "proliferative disorder" and "proliferative disease" are used interchangeably herein and refer to any of a variety of diseases in which cells exhibit uncontrolled growth. Proliferative disorders include all types of cancers or tumors. In preferred embodiments, the proliferative disorders refer to hemopoietic disorders or disorders arising in the blood-forming cells of the bone marrow and lymph system. Examples of such disorders include lymphocytic leukemia, acute myelogenous leukemia, acute lymphoblastic leukemia, myelodysplastic syndrome, chronic myelomonocytic leukemia, juvenile myelomonocyte leukemia, multiple myeloma, lymphoma, T-cell chronic lymphocytic leukemia, prolymphocytic leukemia, prolymphocytic leukemia, hairy cell leukemia, follicular lymphoma, lymphoplasmocytic immunocytoma, plasma cell leukemia, T prolymphocytic leukemia, mycosis fungoides, large granular lymphocyte leukemia, and adult T cell leukemia.

A "test sample" as used herein may be acquired from essentially any diseased or healthy organism, including humans, animals and plants, as well as cell cultures, recombinant cells, cell components and environmental sources. Samples may be from any animal, including by way of example and not limitation, humans, dogs, cats, sheep, cattle, and pigs. Samples can be a biological tissue, fluid or specimen. Methods of obtaining test samples are well known to those of skill in the art and include, but are not limited to, aspirating, tissue sectioning, drawing of blood or other fluids, surgical or needle biopsing, and the like. The test sample may be obtained from an individual or a patient. The test sample may contain cells, tissues or fluid obtained from a patient suspected of having a proliferative disorder. The test sample may be liquid without any cells or tissue. Samples may also be processed, such as sectioning of tissues, fractionation, purification, or cellular organelle separation.

In preferred embodiments, the test sample is a "body fluid" or "bodily fluid." These terms are used interchangeably herein and refer to a fluid sample from a human, animal, or cell culture. Body fluids include, but are not limited to amniotic fluid, blood, cerebrospinal fluid, peritoneal fluid, plasma, pleural fluid, saliva, semen, serum, sputum, tears, and urine.

A "reference sample" comprises a sample of bodily fluid typically from a normal individual or from an individual of a wild-type cell population with a normal CD marker phenotype. In other embodiments, a reference sample may be taken from a patient with a known disease or disorder.

The term "level" as used herein refers to a amount or a concentration of a CD marker. Typically, the level of a CD marker will be expressed as a concentration, or an amount of CD marker per volume or weight.

The term "enzyme linked immunosorbent assay" (ELISA) as used herein refers to an antibody-based assay in which detection of the antigen of interest is accomplished via an enzymatic reaction producing a detectable signal. ELISA can be run as a competitive or non-competitive format. ELISA also includes a 2-site or "sandwich" assay in which two antibodies to the antigen are used, one antibody to capture the antigen and one labeled with an enzyme or other detectable label to detect captured antibody-antigen complex.

In a typical 2-site ELISA, the antigen has at least one epitope to which unlabeled antibody and an enzyme-linked antibody can bind with high affinity. An antigen can thus be affinity captured and detected using an enzyme-linked antibody. Typical enzymes of choice include alkaline phosphatase or horseradish peroxidase, both of which generated a detectable product upon digestion of appropriate substrates.

The term "label" as used herein, refers to any physical molecule directly or indirectly associated with a specific binding agent or antigen which provides a means for detection for that antibody or antigen. A "detectable label" as used herein refers any moiety used to achieve signal to measure the amount of complex formation between a target and a binding agent. These labels are detectable by spectroscopic, photochemical, biochemical, immunochemical, electromagnetic, radiochemical, or chemical means, such as fluorescence, chemifluoresence, or chemiluminescence, or any other appropriate means. Preferred detectable labels include fluorescent dye molecules or fluorophores.

DETAILED DESCRIPTION OF THE INVENTION

Figure 1:
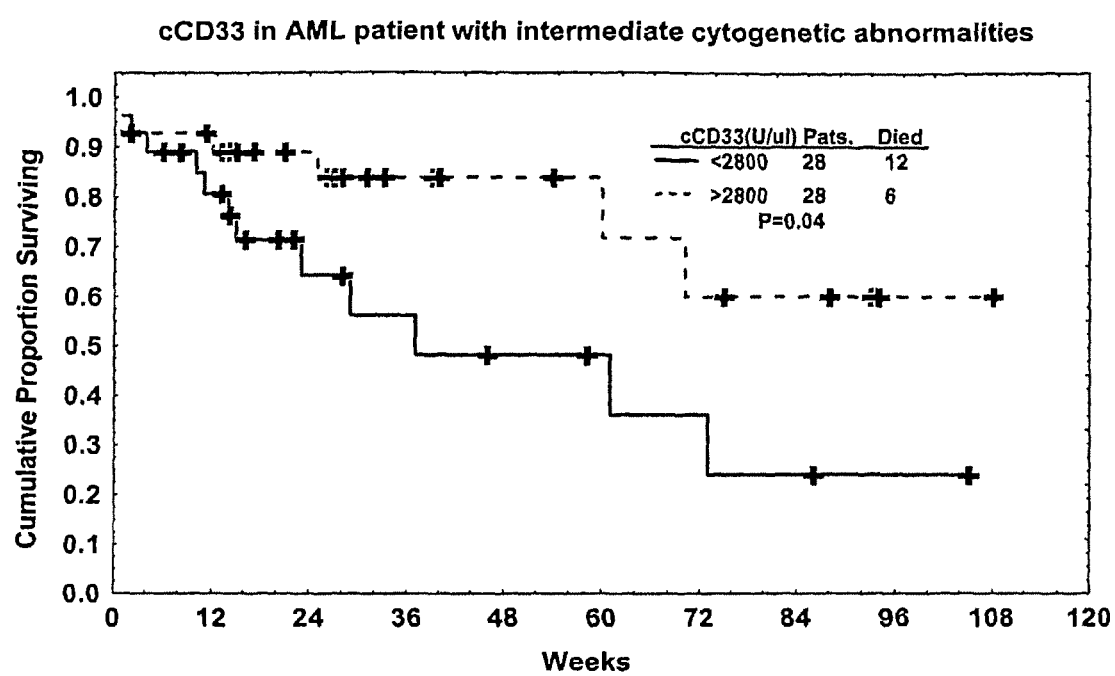
FIG. 1. shows the cumulative proportion of AML patients surviving in two populations of patients: 1) patients having plasma concentration of circulating cell-free CD33 of less than 2,800 U/μL (solid line), and 2) patients having plasma concentration of circulating cell-free CD33 of greater than 2,800 U/μL (dashed line).

In accordance with the present invention there are provided methods of determining the cellular CD phenotype of an individual having a proliferative disorder. The CD phenotype is determined through assaying a sample of bodily fluid from the patient for specific CD markers. CD markers are assayed using assays known in the art and binding agents specific to the markers of interest. The levels of each CD marker are then compared to the levels in a normal individual free from any proliferative disorder. Markers for which the levels deviate from the normal levels are assigned to the phenotype of the patient. This phenotype can then be used for classification of the proliferative disorder and for the determination of prognosis or treatment of the disorder. Further, changes in the levels over time can be used to assess progression of the disorder or success of the treatment thereof.

Antibodies to CD Markers

Methods of generating antibodies are well known in the art, see, e.g., Sambrook, et al., 1989, Molecular Cloning: A Laboratory Manual, Second Edition, Cold Spring Harbor Press, Plainview, NY.

Antibodies may be detectably labeled by methods known in the art. Labels include, but are not limited to, radioisotopes such as $^{125}$I, enzymes (e.g., peroxidase, alkaline phosphatase, beta-galactosidase, and glucose oxidase), enzyme substrates, luminescent substances, fluorescent substances, biotin, and colored substances. In binding these labeling agents to the antibody, the maleimide method (J. Biochem. (1976), 79, 233), the activated biotin method (J. Am. Chem. Soc. (1978), 100, 3585) or the hydrophobic bond method, for instance, can be used.

Antibodies to CD markers are available commercially through multiple sources. For example, purified antibodies directed against numerous human CD markers are available labeled or unlabeled through Caltag Laboratories (Burlingame, CA). In particular, antibodies against human CD3, CD4, CD5, CD8, CD33, CD34, and IL-1β are available from Abeam Inc. (Cambridge, MA). Antibodies against human IL-1Ra have been described previously (see Hammerberg et al., J. Clin. Invest. 90(2):571-583 (1992); Chensue et al., Am. J. Pathol. 140(2):269-275 (1992)).

Immunoassays to Detect CD Markers

Immunoassays, or assays to detect an antigen using an antibody, are well known in the art and can take many forms, e.g., radioimmunoassay, immunoprecipitation, Western blotting, enzyme-linked immunosorbent assay (ELISA), and 2-site or sandwich immuno assay.

In preferred embodiments, a sandwich ELISA is used. In this assay, two antibodies to different segments, or epitopes, of the antigen are used. The first antibody (capture antibody) is coupled to a solid support. When a sample of bodily fluid is contacted with the capture antibody on the solid support, the antigen contained in the bodily fluid is captured on the solid support through a specific interaction between antigen and antibody, resulting in the formation of a complex. Washing of the solid support removes unbound or non-specifically bound antigen. Subsequent exposure of the solid support to a detectably-labeled second antibody (detection antibody) to the antigen (generally to a different epitope than the capture antibody) enables the detection of bound or captured antigen. As would be readily recognized by one of skill in the art, assaying of a plurality of CD markers in parallel is possible with the use of distinct pairs of specific antibodies, each of which is directed against a different CD marker.

Relative or actual amounts of CD markers circulating in body fluids can be determined by methods well known in the art. For example, a standard curve can be obtained in the ELISA using known amounts of the CD markers. The actual amount of the CD marker in a body fluid may thus be determined using the standard curve. Another approach that does not use a standard curve is to determine the dilution of body fluid that gives a specified amount of signal. The dilution at which 50% of the signal is obtained is often used for this purpose. In this case, the dilution at 50% maximal binding of a CD marker in a patient body fluid is compared with the dilution at 50% of maximal binding for the same CD marker obtained in the same assay using a reference sample (i.e., a sample taken from a comparable bodily fluid of a normal individual, free of proliferative disorders). CD markers from the test sample where the dilution at 50% of maximal binding deviates by two fold more preferably three fold, more preferably four fold, more preferably 5 fold, more preferably 6 fold, more preferably 7 fold, more preferably 8 fold, more preferably 9 fold, and even more preferably 10 fold over that for the reference sample are assigned to the phenotype. For example, if the dilution at 50% maximal binding for CD3 in the test sample is two fold or greater than the dilution at 50% maximal binding for CD3 in the reference sample, it can be concluded that the cells which underlie the proliferative disorder in the individual have a CD3$^+$ cell surface phenotype.

Monoclonal or polyclonal antibodies may be used as the capture and detection antibodies in sandwich ELISA systems. Monoclonal antibodies are specific for single epitope of an antigen and allow for detection and quantitation of small differences in antigen. Polyclonal antibodies can be used as the capture antibody to capture large amounts of antigen or can be used as the detection antibody. A monoclonal antibody can be used as the either the capture antibody or the detection antibody in the sandwich assay to provide greater specificity. More typically, polyclonal antibodies are used as the capture antibody and monoclonal antibodies are used as the detection antibody.

One consideration in designing a sandwich ELISA is that the capture and detection antibodies should be generated against or recognize "non-overlapping" epitopes. The phrase "non-overlapping" refers to epitopes, which are segments or regions of an antigen that are recognized by an antibody, that are sufficiently separated from each other such that an antibody for each epitope can bind simultaneously. That is, the binding of one antibody (e.g., the capture antibody) to a first epitope of the antigen should not interfere with the binding of a second antibody (e.g., the detection antibody)

to a second epitope of the same antigen. Capture and detection antibodies that do not interfere with one another and can bind simultaneously are suitable for use in a sandwich ELISA.

Methods for immobilizing capture antibodies on a variety of solid surfaces are well-known in the art. The solid surface may be composed of any of a variety of materials, for example, glass, quartz, silica, paper, plastic, nitrocellulose, nylon, polypropylene, polystyrene, or other polymers. The solid support may be in the form of beads, microparticles, microspheres, plates which are flat or comprise wells, shallow depressions, or grooves, microwell surfaces, slides, chromatography columns, membranes, filters, or microchips. In a preferred embodiment, the solid support is a microwell plate in which each well comprises a distinct capture antibody to a specific CD marker so that multiple markers may be assayed on a single plate. In another preferred embodiment, the solid support is in the form of a bead or microparticle. These beads may be composed of, for example, polystyrene or latex. Beads may be of a similar size or may be of varying size. Beads may be approximately 0.1 μm-10 μm in diameter or may be as large as 50 μm-100 μm in diameter.

Methods of identifying the binding of a specific binding agent to a CD marker are known in the art and vary dependent on the nature of the label. In preferred embodiments, the detectable label is a fluorescent dye. Fluorescent dyes are detected through exposure of the label to a photon of energy of one wavelength, supplied by an external source such as an incandescent lamp or laser, causing the fluorophore to be transformed into an excited state. The fluorophore then emits the absorbed energy in a longer wavelength than the excitation wavelength which can be measured as fluorescence by standard instruments containing fluorescence detectors. Exemplary fluorescence instruments include spectrofluorometers and microplate readers, fluorescence microscopes, fluorescence scanners, and flow cytometers.

In a preferred embodiment, a sandwich assay is constructed in which the capture antibody is coupled to a solid support such as a bead or microparticle. Captured antibody-antigen complexes, subsequently bound to detection antibody are detected using flow cytometry and is well-known in the art. Flow cytometers hydrodynamically focus a liquid suspension of particles (e.g., cells or synthetic microparticles or beads) into an essentially single-file stream of particles such that each particle can be analyzed individually. Flow cytometers are capable of measuring forward and side light scattering which correlates with the size of the particle. Thus, particles of differing sizes may be used in invention methods simultaneously to detect distinct CD markers. In addition, fluorescence at one or more wavelengths can be measured simultaneously. Consequently, particles can be sorted by size and the fluorescence of one or more fluorescent labels can be analyzed for each particle. Exemplary flow cytometers include the Becton-Dickenson Immunocytometry Systems FACSCAN. Equivalent flow cytometers can also be used in the invention methods.

The invention will now be described in greater detail by reference to the following non-limiting examples.

Example 1

Determination of a CD Phenotype in a Patient Having a Proliferative Disorder

Antibodies to CD markers, for example, CD3, CD4, CD5, CD7, and CD8, are obtained through commercial sources and are immobilized in distinct wells of a 96-well clear methacrylate microplate by the following process. The antibody to be coated onto the plate is diluted to a concentration of 2-10 μg/ml in a buffer such as phosphate buffered saline (PBS) and added to each well at a volume of about 100 μl per well. The plate is incubated for 18-20 hours at room temperature or 4° C. The unoccupied sites are blocked with a blocking agent (200-300 μl/well) such as bovine serum albumin (BSA).

A test sample of bodily fluid from a patient with a proliferative disorder is serially diluted and added to each well (50-100 μl/well). The plate is incubated for one or more hours. The wells are washed using PBS with 0.05% Tween 20. A second antibody to the same CD marker which is labeled with horse radish peroxidase (HRP) and is compatible with the first antibody (i.e. the two antibodies can be used together in a two site assay) is diluted in blocking buffer then added to each well (100-200 μl/well) and incubated for 1 hour. The wells are washed to removed unbound labeled antibody.

100 μL of QuantaBlu™ fluorogenic peroxidase substrate (Pierce Biotechnology, Rockford IL) is added to each well. The plate is incubated at room temperature for 60 minutes and the reaction stopped by addition of 100 μL of QuantaBlu™ Stop Solution (Pierce Biotechnology, Rockford IL) prior to fluorescence measurement. Horseradish peroxidase activities of each dilution are measured at the excitation wavelength of 330 nm and the emission wavelength of 425 nm using a Packard FluoroCount microplate fluorometer with a standard light source in bottom-reading mode. The concentration of the CD marker in the test sample of bodily fluid is determined by comparing to a standard curve standard curve of known concentrations of CD marker versus fluorescence signal obtained using the same method.

Once the concentration of each CD marker assayed has been determined, these concentrations are compared to the concentration of the corresponding CD marker in a bodily fluid sample from a normal individual. Those CD markers with concentrations above the concentration in a normal individual are assigned to the CD marker phenotype. For example, if a test sample has increased concentrations of markers CD3 CD4, CD5, and CD7 but an equivalent concentration of CD8 as compared with the concentration in a normal individual, the CD phenotype would be CD3 CD4, CD5, and CD7.

Example 2

Identification of a Tumor Type Using the CD Phenotype

The CD phenotype of a proliferative disorder determined using body fluid as described in Example 1 is used to classify the type of proliferative disorder in the individual by comparison to known cell surface CD marker phenotypes. For example, Table 1 and Table 2 provide cell-surface CD marker phenotypes for exemplary types of leukemias. The particular CD phenotype determined in a body fluid from an individual with a proliferative disorder can be compared to the table to identify the classification of the proliferative disorder. For example, if a phenotype is determined in a body fluid sample from an individual with a proliferative disorder to have increased levels in the fluid of CD3 CD4, CD5, and CD7, it can be concluded using the Table 2 that the individual has adult T cell leukemia.

TABLE 1

Cell-surface expression of markers in leukemic B-cell proliferative disorders.

| Antigen | CLL | PLL | HCL | FL | MCL | LP-IC | PCL |
|---|---|---|---|---|---|---|---|
| | | | | Diagnosis | | | |
| CD5 | + | -/+w | - | - | + | +/- | - |
| CD10 | - | - | - | +/- | - | - | -/+ |
| CD11c | +/-w | -/+ | +s | - | - | -/+ | - |
| CD19 | + | + | + | + | + | + | - |
| CD20 | + | + | + | + | >+ | + | - |
| CD23 | + | -/+ | - | -/+ | - | -/+ | - |
| CD38 | - | - | -/+w | -/+w | - | +/- | +s |
| CD103 | - | - | +s | - | - | - | - |

TABLE 1 shows the cell-surface expression of markers in examples of leukemic B-cell proliferative disorders. Abbreviations used therein include: CLL, chronic lymphocytic leukemia; PLL, prolymphocytic leukemia; HCL, hairy cell leukemia; FL, follicular lymphoma; MCL, mantle cell lymphoma; LP-IC, lymphoplasmocytic immunocytoma; PCL, plasma cell leukemia. Level of expression are shown as: -, antigen not expressed; -/+, antigen expressed in less than 50% of patients; +/-, antigen expressed in majority of patients; +, antigen expressed; w, weak expression; s, strong expression.

TABLE 2

Cell-surface expression of markers in leukemic T-cell proliferative disorders.

| Antigen | T-PLL | Sézary/MF | LGLL | ATL |
|---|---|---|---|---|
| | | Diagnosis | | |
| CD3 | + | + | + | + |
| CD4 | +/- | + | -/+ | + |
| CD5 | + | + | + | + |
| CD7 | + | - | -/+ | -/+ |
| CD8 | -/+ | - | +/- | - |
| CD56 | - | - | +/- | - |
| CD57 | - | - | +/- | - |

TABLE 2 shows the cell-surface expression of markers in examples of leukemic T-cell lymphoproliferative disorders. Abbreviations used therein include: T-PLL, T prolymphocytic leukemia; MF, mycosis fungoides; LGLL, large granular lymphocyte leukemia; ATL, adult T cell leukemia. Level of expression are shown as: -, antigen not expressed; -/+, antigen expressed in less than 50% of patients; +/-, antigen expressed in majority of patients; +, antigen expressed; w, weak expression; s, strong expression.

Example 3

Monitoring of Treatment or Disease Progression

To monitor disease progression in the case of a proliferative disorder, bodily fluid samples from a patient are tested at two points in time (i.e., a first test sample and a second test sample). A sample is obtained prior to treatment (first test sample) and following treatment (second test sample) and evaluated to determine the concentration of CD markers as described in Example 1. An increase in the concentration of CD markers in the second test sample, as compared to the first test sample, indicates progression of the disease whereas a decrease in the concentration of CD markers in the second sample versus the first test sample indicates a regression of the disease.

Example 4

Circulating Cell-Free CD33 in Patients with Acute Myeloid Leukemia and Myelodysplastic Syndrome CD33, a 67-kDa sialoglycoprotein expressed on the cell surface of monocytic/myeloid lineage and early hematopoietic progenitor cells, is frequently expressed in patients with acute myeloid leukemia (AML). A bead-based immunoassay was used to measure circulating cell-free CD33 (cCD33) in the plasma of patients with AML (n=97) or myelodysplastic syndrome (MDS; n=44). All patients were treated with standard therapy including idarubicin and ara-C. cCD33 levels were significantly higher in patients with MDS (median, 1600 U/μL; range, 102-791,350 U/μL) than in those with AML (median, 2,709 U/μL; range: 62-263,349 U/μL) (P=0.004). High-risk cytogenetic abnormalities were associated with higher cCD33 levels in patients with MDS (P=0.04) but not in patients with AML (P=0.72). cCD33 levels correlated with WBC count and % monocytes in patients with AML (R>0.35) but not in patients with MDS. cCD33 levels correlated with clinical behavior only among AML patients with intermediate-risk cytogenetic abnormalities (n=56); those with cCD33 levels above the median had longer survival (P=0.04) (FIG. 1). These data confirm the presence of cCD33 in AML and MDS and also suggest that cCD33 can be used as a tumor marker in patients with AML.

Example 5

Circulating Cell-Free CD3 and CD5 in Patients with Chronic Lymphocytic Leukemia

CD5 is a transmembrane protein expressed in T-cells, few B-cells and chronic lymphocytic leukemia B-cells. CD5 has been shown to be part of the T-cell receptor (TCR)-CD3 complex in T-cells as well as the B cell receptor (BCR) complex and serves as substrate for tyrosine kinase activity induction. A bead-based sandwich immunoassay was used to measure circulating cell-free CD3 (cCD3) and circulating cell-free CD5 (cCD5) in the plasma of 85 patients with chronic lymphocytic leukemia (CLL) and 51 normal controls. The values of cCD5 were examined alone as a tumor marker in CLL as well as after normalization to the values of cCD3. Both cCD3 and cCD5 were significantly higher in patients with CLL (medians, 7,465 and 55,806 U/μL, respectively) as compared with normal control (Medians, 830 and 1,671 U/μL, respectively). Patients with CLL had significantly higher relative cCD5:cCD3 (median, 5.28; range, 0-161 fold) as compared with normal control (median, 1.70; range, 0-8.06 fold). Levels of cCD5, but not cCD3 correlated positively (P<0.01) with WBC, β2-microglobulin, splenomegaly, and Rai stage. Relative cCD5:cCD3 levels also correlated with Rai stage (P=0.04) and β2-microglobulin (0.03). Both cCD5 levels and relative ratio of cCD5:cCD3 correlated with survival (P=0.03). These findings confirm that the free circulating surface markers CD3 and CD5 can be detected in the circulation of patients with CLL and most likely reflect the tumor load and can be used as a tumor marker.

Example 6

Figure 2:
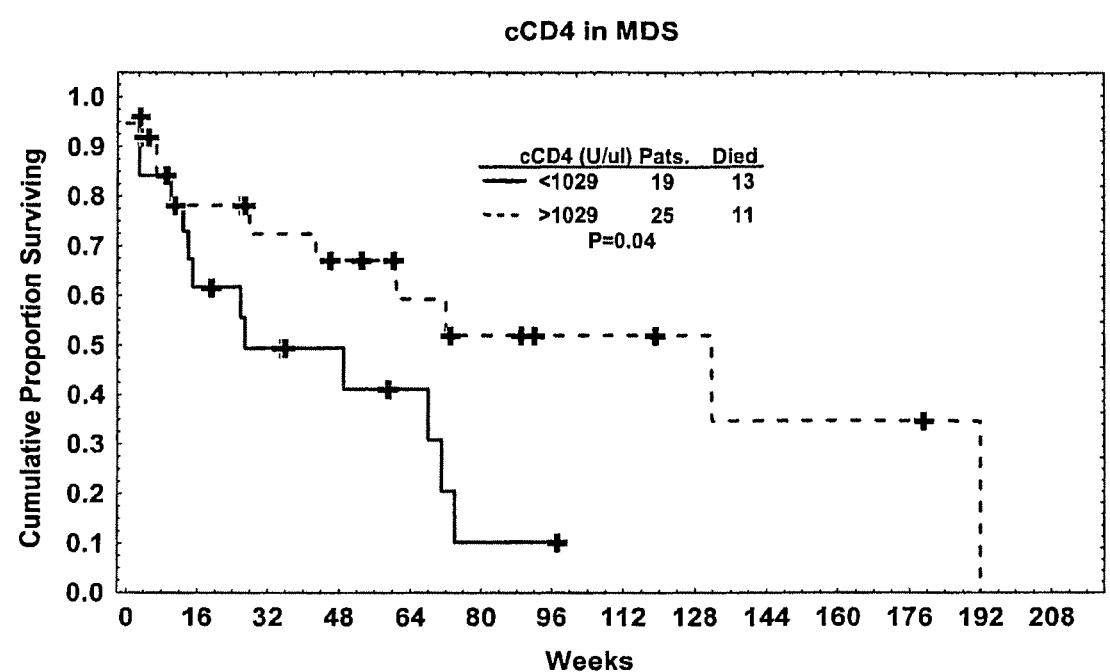
FIG. 2. shows the cumulative proportion of MDS patients surviving in two populations of patients: 1) patients having plasma concentration of circulating cell-free CD4 of less than 1,029 U/μL (solid line), and 2) patients having plasma concentration of circulating cell-free CD4 of greater than 1,029 U/μL (dashed line).

Circulating Cell-Free CD4 and CD8 in Patients with Acute Myeloid Leukemia and Myelodysplastic Syndrome CD4 is a 55-kDa glycoprotein expressed mainly on the surface of helper/inducer T-cells and monocyte-derived cells. CD4 responds to antigen associated with MHC class II. CD8 is a disulfide-linked dimer of either an alpha- and a beta-chain or two alpha-chains (34 kDa each). CD8 is expressed on T-cytotoxic/suppressor cells and binds to antigen associated with MHC class I. A bead-based sandwich immunoassay was used to measure circulating cell-free CD4 (cCD4) and circulating cell-free CD8 (cCD8) in the plasma of 98 patients with AML and 50 patients with MDS and assessed associations with clinical behavior. Whereas cCD4 levels did not differ significantly between AML (median, 918 U/µL; range, 0-30,038 U/µL) and MDS (median, 1,029 U/µL; range, 0-48,338 U/µL in MDS), cCD8 levels were significantly higher in AML (median, 120390 U/µL; range, 0-694820 U/µL) than in MDS (median, 105340 U/µL; range, 0-810110 U/µL) (P=0.03). The ratio of cCD4 to cCD8 was significantly higher in AML and MDS than in 51 normal controls (P<0.01). There was no correlation between cCD4 or cCD8 and clinical response or survival in AML patients. In MDS, Cox regression analysis showed that higher levels of cCD4 correlated with longer survival when considered as a continuous variable (P=0.03) and when the median was considered as a cut-point (P=0.04) (FIG. 2). MDS patients with high levels of cCD4 (>929 U/µL) also had longer remission duration (P=0.01); there was no correlation between cCD8 levels and clinical behavior.

Example 7

Figure 3:
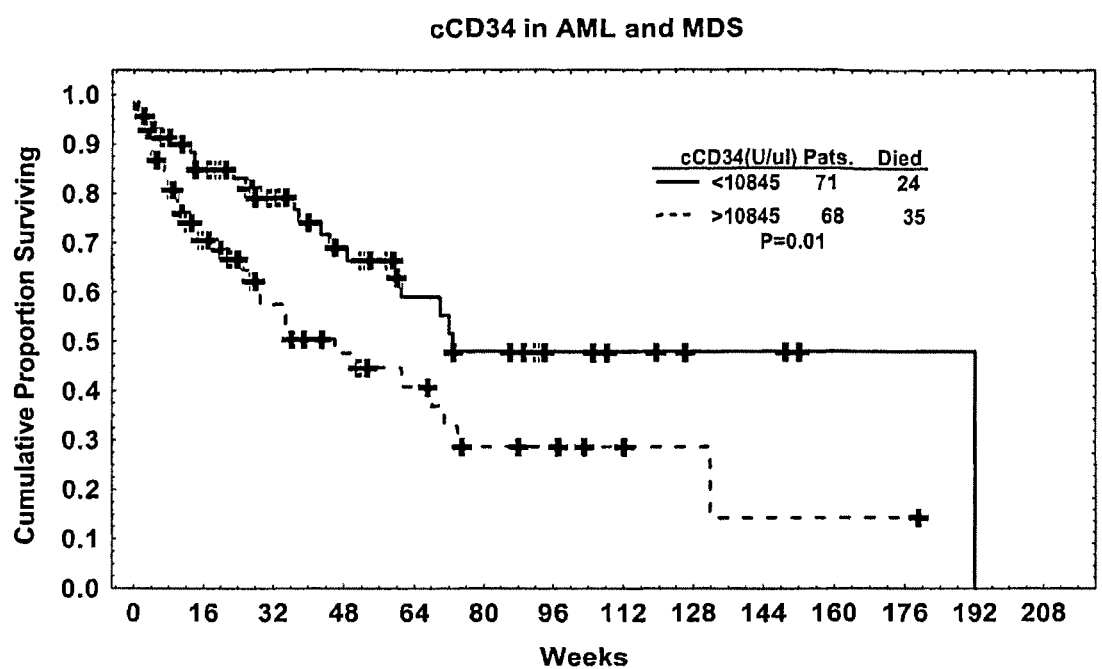
FIG. 3. shows the cumulative proportion of AML and MDS patients surviving in two populations of patients: 1) patients having plasma concentration of circulating cell-free CD34 of less than 10,845 U/μL (solid line), and 2) patients having plasma concentration of circulating cell-free CD33 of greater than 10,845 U/μL (dashed line).

Circulating Cell-Free CD34 in Patients with Acute Myeloid Leukemia and Myelodysplastic Syndrome CD34 is an approximately 116-kd glycophosphoprotein expressed in hematopoietic progenitor cells, endothelial cells, and some mesenchymal and neural cells. CD34 is a typical adhesion molecule capable of inducing the cell signal transduction pathway leading to adhesion and differentiation. A bead-based assay was used to measure cell-free circulating cell-free CD34 (cCD34) in the plasma of patients with acute myeloid leukemia (AML; n=98) and myelodysplastic syndrome (MDS; n=50). Levels of cCD34 were significantly higher in AML (median 10983, range: 844-100, 4191 U/10 µL) than in MDS (median: 8749, range: 102-791,350 U/10 µL) patients (P<0.01). cCD34 levels were higher among patients with high-risk cytogenetic abnormalities in AML (P=0.01) but not MDS (P=0.92). When grouped together, AML and MDS patients with cCD34 levels higher than the median (10,845 U/µL) had significantly shorter survival than those with lower levels (P=0.01) (FIG. 3). This association was independent of cytogenetic grouping, age, and performance status. cCD34 levels did not correlate with percent of blasts or CD34+ cells but did correlate with WBC count (R=0.36) in patients with AML, suggesting that cCD34 reflects the overall leukemia load.

Example 8

Interleukin-1 Receptor Antagonist and Interleukin-1 Beta in Patients with Chronic Lymphocytic Leukemia Interleukin-1 receptor antagonist (IL-1Ra) is a 23-KDa soluble glycoprotein that blocks the activity of IL-1α and IL-1β by competing with type I and type II IL-1 receptors without initiating signal transduction. IL-1Ra is anti-inflammatory, while IL-1β is a proinflammatory molecule. IL-1β enhances the immunological and hemopoietic systems and IL-1Ra acts as an inhibitor. IL-1β induces the cell surface expression of cytokine receptors on lymphoid and hemopoietic cells, whereas IL-1Ra suppresses this activity. IL-1β augments lymphoid and hemopoietic cell growth, whereas IL-1Ra suppresses this growth. IL-1Ra and IL-1β levels were measured in the plasma of 92 patients with chronic lymphocytic leukemia (CLL). IL-1Ra levels were significantly higher in CLL patients (median, 389, range 52-3,667 pg/mL) than in 31 normal control subjects (median, 217; range, 94-868 pg/mL) (P<0.001). In contrast, IL-1β levels were significantly lower in CLL patients (median, 2.23; range, 1.89-12 pg/mL) than in normal controls (median, 2.68; range, 2.08-5.5) (P<0.01). Overall, neither IL-1Ra nor IL-1β correlated significantly with WBC count, β2-microglobulin (β2-M) level, Rai stage, platelet count, mutation status, or treatment history. Only age correlated with IL-1Ra (R=0.39, P<0.001). Using a univariate Cox proportional hazards model, a direct correlation with survival was found when IL-1Ra was used as a continuous variable (P<0.001). This association was independent of Rai stage, β-2M, and IgVH mutation status. However, in a multivariate analysis incorporating a combination of IgVH, β2-M, and IL-1Ra, IL-1Ra was no longer a predictor of survival. When patients were dichotomized according to the median IL-1Ra level, those with higher levels had longer survival (P=0.057). In contrast, IL-1β did not correlate with survival (P=0.14). These data suggest that IL-1Ra, but not IL-1β, plays a role in the biology of CLL and that the stronger the anti-inflammatory process in CLL, the more aggressive the disease.

The contents of the articles, patents, and patent applications, and all other documents and electronically available information mentioned or cited herein, are hereby incorporated by reference in their entirety to the same extent as if each individual publication was specifically and individually indicated to be incorporated by reference.

Applicants reserve the right to physically incorporate into this application any and all materials and information from any such articles, patents, patent applications, or other physical and electronic documents.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other embodiments are within the following claims. In addition, where features or aspects of the invention are described in terms of Markush groups, those skilled in the art will recognize that the invention is also thereby described in terms of any individual member or subgroup of members of the Markush group.

That which is claimed is:

1. A method for detecting one or more circulating cell-free markers in a patient with chronic lymphocytic leukemia (CLL), the method comprising:
   (a) assaying a bodily fluid sample from a patient diagnosed as having CLL to determine the level of a circulating cell-free CD5 (cCD5) and circulating cell-free IL-1Ra (IL-Ra) in the sample, wherein assaying comprises
      (i) contacting the bodily fluid sample with an antibody specific for CD5 and an antibody specific for IL-1Ra
      (ii) selectively enriching the bodily fluid sample with the antibodies, and
      (iii) detecting the level of the cCD5 and the circulating IL-1Ra, and
   (b) identifying the patient as
      (i) having a shorter survival duration if the cCD5 and the cell-free IL-1Ra are enriched in the fluid sample and at least the level of the cell-free IL-1Ra is determined to be less than 389 pg/mL, whereby the cell-free IL-1Ra level less than 389 pg/mL indicates that the patient will have a shorter survival duration compared to a patient that has the cell-free IL-1Ra level more than 389 pg/mL; or
      (ii) having a longer survival duration if the cCD5 and the cell-free IL-1Ra are enriched in the fluid sample and at least the level of the cell-free IL-1Ra is determined to be more than 389 pg/mL, whereby the cell-free IL-1Ra level more than 389 pg/mL indicates that the patient will have a longer survival duration compared to a patient that has the cell-free IL-1Ra level less than 389 pg/mL.

2. The method of claim 1, further comprising assaying the bodily fluid sample of step (a) to determine the level of circulating cell-free CD3 (cCD3).

3. The method of claim 2, further comprising determining a cCD5:cCD3 ratio.

4. The method of claim 1, wherein the bodily fluid is selected from the group consisting of blood, plasma, serum, lymphatic fluid, cerebrospinal fluid, synovial fluid, urine, and saliva.

5. The method of claim 1, wherein the antibody has a detectable label.

6. The method of claim 5, wherein the label is selected from the group consisting of a radioisotope, an enzyme, an enzyme substrate, a luminescent substance, a fluorescent substance, biotin, and a colored substance.

7. The method of claim 1, wherein assaying comprises performing a process selected from the group consisting of a sandwich immunoassay, a radioimmunoassay, immunoprecipitation, Western blotting, and an enzyme-linked immunosorbent assay.

8. A detection method comprising:
   (a) obtaining a bodily fluid sample from a subject diagnosed as having chronic lymphocytic leukemia (CLL),
   (b) contacting the bodily fluid sample with an antibody specific for CD5 and an antibody specific for IL-1Ra,
   (b) testing the bodily fluid sample for circulating cell-free CD5 (cCD5),
   (c) testing the bodily fluid sample for circulating cell-free IL-1Ra, and
   (d) detecting in the fluid sample the level of cCD5 and the level of cell-free IL-1Ra by an immunoassay.

9. The detection method of claim 8, wherein the subject has a longer survival duration when the level of cell-free IL-1Ra is more than 389 pg/mL and the subject has a shorter survival duration when the level of cell-free IL-1Ra is less than 389 pg/mL.

10. The detection method of claim 8, wherein the antibodies have a detectable label.

11. The detection method of claim 10, wherein the detectable label is selected from the group consisting of a radioisotope, an enzyme, an enzyme substrate, a luminescent substance, a fluorescent substance, biotin, and a colored substance.

* * * * *